United States Patent

Harada et al.

[11] Patent Number: 4,497,742
[45] Date of Patent: Feb. 5, 1985

[54] ISOMERIZATION OF β-LACTAM COMPOUNDS

[75] Inventors: Setsuo Harada, Kawanishi; Shigetoshi Tsubotani, Suita; Mitsuko Asai, Takatsuki, all of Japan

[73] Assignee: Takeda Chemical Industries, Ltd., Osaka, Japan

[21] Appl. No.: 351,927

[22] Filed: Feb. 24, 1982

[30] Foreign Application Priority Data

Mar. 4, 1981 [JP] Japan .................................. 56-31866
Jan. 22, 1982 [JP] Japan .................................. 57-9249

[51] Int. Cl.³ ..................... C07D 487/04; A61K 31/40
[52] U.S. Cl. ............................................. 260/245.2 T
[58] Field of Search .................. 260/245.2 T, 245.2 R; 424/274

[56] References Cited

U.S. PATENT DOCUMENTS 4,278,686  7/1981  Corbett et al. ............... 260/245.2 T
4,374,144  2/1983  Corbett ....................... 260/245.2 T

FOREIGN PATENT DOCUMENTS 8885     of 0000  European Pat. Off. .
0047611  3/1982   European Pat. Off. .
3003624  of 0000  Fed. Rep. of Germany .
57-11982 1/1982   Japan ........................... 260/245.2 T Primary Examiner—Nicholas S. Rizzo
Attorney, Agent, or Firm—Wenderoth, Lind & Ponack

[57] ABSTRACT

Compounds of the formula (I):

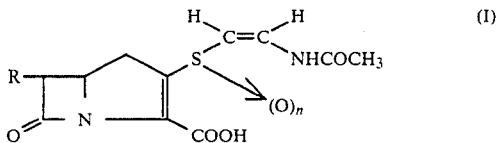

wherein R is an ethyl group which may optionally be substituted and n is 0 or 1, or a physiologically acceptable salt thereof, can be produced by subjecting to isomerization a compound of the formula (II):

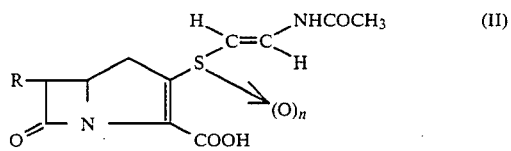

wherein R and n have the same meaning as defined above, or a salt thereof, by using a quaternary ammonium halide and are useful as a bactericide or disinfectant, and also a synergistic effect with penicillin and/or cephalosporin antibiotic agents.

Among the compounds of the formula (I), compounds shown by the formula:

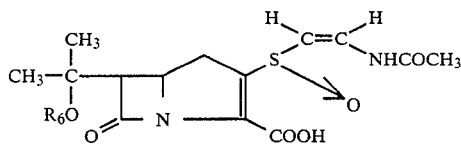

wherein $R_6$ is H or $-SO_3H$, as well as salts thereof, are novel.

3 Claims, No Drawings

ISOMERIZATION OF β-LACTAM COMPOUNDS

The present invention relates to a method of producing compounds of the following formula (I), or physiologically acceptable salts thereof, which have high antimicrobial activity and β-lactamase inhibitory activity.

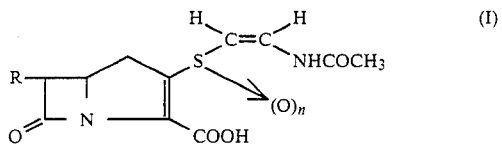

wherein R is an ethyl group which may optionally be substituted and n is 0 or 1.

In accordance with the present invention, a compound of the above formula (I) or a physiologically acceptable salt thereof (which will also be referred to sometimes as compound (I) hereinafter) can be produced by subjecting to isomerization a compound of the formula (II):

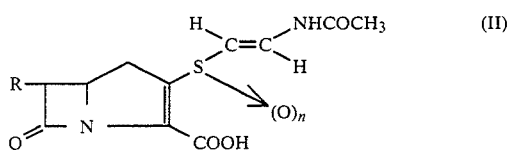

wherein R and n have the same meaning as defined above, or a salt thereof (which will also be referred to sometimes as compound (II) hereinafter) by using a quaternary ammonium halide. The isomerization is preferably carried out in an organic solvent. However, solvents of strong polarity, for example methanol and dimethylformamide, are not suitable for the reaction.

The principle of the above reaction may be explained as follows. The compound (II) is invariably a water-soluble substance and as such cannot be extracted into a nonpolar solvent by the usual extraction procedure. However, if the compound (II) exists together with an excess of a quaternary ammonium halide, the sulfonyloxy group or/and carboxy group which are responsible for the water solubility of compound (II) form quaternary ammonium salts, whereby the lipophilicity of the whole molecule increases to the extent that the compound (II) migrates into a nonpolar medium. And the excess ammonium halide acts selectively on the double bond in the side chain so that the compound (II) of E(trans-)configuration is transferred in good yield into the compound (I) of Z(cis-)configuration. As to the addition reaction of the ammonium halide to the sulfonyloxy group and carboxy group, the addition to the sulfonyloxy group takes place preferentially owing to the relative acidity of these groups.

The quaternary ammonium halide useful for the purposes of the present invention includes compounds which are commonly used in ion-paired extraction, i.e. the chlorides or bromides of quaternary ammonium compounds having a total of about 18 to 30 carbon atoms for the four substituents (e.g. alkyls of 1 to 25 carbon atoms, benzyl, etc.), such as tetra-n-pentylammonium, tetra-n-hexyl-ammonium, tri-n-octylmethylammonium, di-n-octylmethylammonium, di-n-decyldimethylammonium, n-hexadecylbenzyldimethylammonium, n-tetradecylbenzyldimethylammonium, etc. although the chlorides are more satisfactory in the efficiency of extraction and the yield of the reaction.

Such a quanternary ammonium halide is used in stoichiometric excess, generally in a proportion of 3 to 1000 molar equivalents based on starting compound (II), preferably in a proportion of 100 to 1000 molar equivalents based on compound (II) which does not possess sulfonyloxy group and in a proportion of 3 to 100 molar equivalents based on starting compound (II) possessing sulfonyloxy group.

The organic solvent mentioned above includes chloroform, dichloromethane, 1,2-dichloroethane, 1,1,1-trichloroethane, benzene, toluene, ethyl acetate, diisopropyl ether, etc., although such halogenated hydrocarbon as chloroform, dichloromethane and 1,2-dichloroethane are most advantageous. In general, a nonpolar solvent or solvent of weak polarity is preferably employed. However, the reaction is not interfered with by the presence of a small proportion of solvents of strong polarity such as methanol, dimethylformamide, tetrahydrofuran, etc. in said organic solvents. The organic solvent is generally used in such a proportion that the concentration of said quaternary ammonium halide in the organic solvent is about 0.5 to 3 percent. While the reaction is carried out at a temperature near the boiling point of the solvent, it proceeds even at room temperature (ca. 15° C.). The range of 40° to 70° C. is especially advantageous. The reaction goes to completion in about 30 minutes to 3 days, although the time varies with the temperature and the type of solvent used.

To isolate the product compound (I) from the reaction mixture, the quaternary ammonium salt of compound (I) and the quaternary ammonium halide in the reaction mixture are extracted, for example with an aqueous solution of sodium iodide or potassium iodide, whereby the sodium or potassium salt of compound (I) and the quaternary ammonium iodide are separated into the aqueous layer and the organic solvent layer, respectively. When a quaternary ammonium chloride is employed, it is possible to employ sodium bromide or potassium bromide, for instance.

The aqueous layer containing the compound (I) can then be separated from the starting compound (II), for example by chromatography. Suitable chromatographic systems for this purpose may involve the use of a high porous resin HP-20 (Mitsubishi Chemical Industries, Japan), a basic ion exchange resin Sephadex QAE-25 (Cl-form, Pharmacia, Sweden) or activated carbon (Takeda Chemical Industries, Ltd., Japan) as a support in conjunction with water, a suitable aqueous solution of methanol or butanol, or an aqueous solution containing a suitable inorganic salt as an eluent.

Referring to the formulas (I) and (II), R is an ethyl group which may optionally be substituted, for example, a group of the formula (III):

{$R_1$ is H or methyl; $R_2$ is H, OH, $R_3COO$-[$R_3$ is $R_4$ or $-NHR_4$ ($R_4$ is alkyl, alkenyl, phenyl, or alkyl substituted by phenyl or phenyloxy; provided that said phenyl may optionally be substituted by lower alkyl, alkoxy or halogen)] or $R_5O_3SO$—($R_5$ is H or lower alkyl)}. The alkyl $R_4$ is preferably a group of 1 to 6 carbon atoms such as methyl, ethyl, propyl, butyl, pentyl, hexyl, etc. The lower alkyls $R_4$ and $R_5$ each is preferably a group of up to 3 carbon atoms, such as methyl and ethyl. The alkenyl $R_4$ is a group of up to 6 carbon atoms, such as vinyl, propenyl, butenyl, pentenyl, hexenyl, etc. The alkoxy $R_4$ is a group of up to 3 carbon atoms, i.e. methoxy, ethoxy and propoxy. The halogen $R_4$ is preferably chloro or fluoro.

These starting compounds are described in the specification of Japanese Unexamined Patent Laid-Open No. 144394/1979 and the literature listed in Table 1, or can be prepared from the compounds listed in Table 1 by the method described in the specification of Japanese Unexamined Patent Laid-Open No. 144394/1979.

TABLE 1

| Code | Name of Compound | Structural Formula $R_2$ | $R_1$ | n | Reference |
|---|---|---|---|---|---|
| IIa | C-19393H$_2$ | OH | CH$_3$ | 1 | (1) |
| IIb | C-19393S$_2$ | OSO$_3$H | CH$_3$ | 1 | (2) |
| IIc | C-19393E$_5$ | OH | H | 1 | (3) |
| IId | MM4550 | OSO$_3$H | H | 1 | (4) |
| IIe | Epithienamycin B | OH | H | 0 | (5) |
| IIf | MM13902 | OSO$_3$H | H | 0 | (4) |
| IIg | C-19393H$_2$M-1 | OH | CH$_3$ | 0 | (6) |
| IIh | C-19393S$_2$M-1 | OSO$_3$H | CH$_3$ | 0 | (7) |
| IIi | Epithienamycin D | OH | H | 0 | (5) |
| IIj | C-19393 iso-H$_2$ | OH | CH$_3$ | 1 | |
| IIk | C-19393 iso-S$_2$ | OSO$_3$H | CH$_3$ | 1 | |

Reference
(1) Japanese Unexamined Patent Laid-Open No. 5496/1981
(2) Japanese Unexamined Patent Laid-Open No. 104296/1980
(3) Production Example 1, which appears hereinafter. (Japanese Patent Application No. 185450/1980)
(4) The Journal of Antibiotics 32 295 (1979)
(5) Japanese Unexamined Patent Laid-Open No. 131596/1977
(6) Production Example 2, which appears hereinafter. (Japanese Patent Application No. 30702/1980)
(7) Production Example 3, which appears hereinafter. (Japanese Patent Application No. 30701/1980)

The structural formulas of compounds (I) obtainable by isomerization of compounds (II) are sometimes designated by the codes given in Table 2.

TABLE 2

| Code | Structural Formula $R_2$ | $R_1$ | n | Reference |
|---|---|---|---|---|
| Ia | OH | CH$_3$ | 1 | |
| Ib | OSO$_3$H | CH$_3$ | 1 | |
| Ic | OH | H | 1 | (8) |
| Id | OSO$_3$H | H | 1 | (8) |
| Ie | OH | H | 0 | (8) |
| If | OSO$_3$H | H | 0 | (8) |
| Ig | OH | CH$_3$ | 0 | |
| Ih | OSO$_3$H | CH$_3$ | 0 | |
| Ii | OH | H | 0 | (8) |
| Ij | OH | CH$_3$ | 1 | |
| Ik | OSO$_3$H | CH$_3$ | 1 | |

References:
(8) Japanese Unexamined Patent Laid-Open No. 38371/1980

The above-mentioned compounds (I) and (II) can be fractionally assayed by high-performance liquid chromatography (briefly, HPLC) using Microbondapak C$_{18}$ or Radial Pak A (Waters Associates Inc., U.S.A.) as a support, methanol-0.02M phosphate buffer (pH 6.3) as a mobile phase, and a UV (254 nm) detector. The Rt values are shown in the examples which appear hereinafter.

In the context of the present invention, the salts of compounds (I) and (II) include the salts of alkali metals such as sodium, potassium, etc. and of alkaline earth metals such as magnesium, calcium, etc.

Among the compounds obtainable by the method of this invention, compounds which may be represented by the formula (IV):

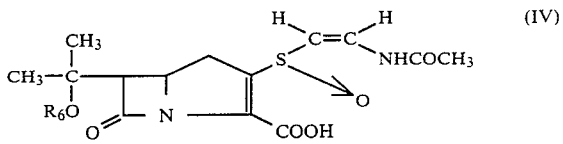

wherein $R_6$ is H or —SO$_3$H, as well as salts thereof, are novel compounds.

The product compounds (I) of this invention are valuable compounds which are active against various gram-positive and gram-negative bacteria and have a strong $\beta$-lactamase-inhibitory activity. These compounds are remarkably superior to the starting compounds in stability in mouse kidney homogenate and, thanks to their increased stability in body fluids, can be expected to display potent therapeutic effects. The antimirobial spectra and inhibitory activities of the compounds according to this invention are shown below.

| (1) | Antimicrobial spectrum [MIC ($\mu$g/ml)] | | | | |
|---|---|---|---|---|---|
| | | Compound | | | |
| | Test Organism | Ia | Ib | Ig | Ih |
| | Escherichia coli NIHJ J2C | 0.78 | 20 | 2.5 | 40 |
| | Proteus vulgaris IFO 3988 | 6.25 | 40 | 5.0 | <40 |
| | Salmonella typhimurium IFO 12529 | 1.56 | 20 | 2.5 | 20 |
| | Staphylococcus aureus FDA 209P | 0.39 | 2.5 | 0.625 | 2.5 |
| (2) | beta-Lactamase-inhibitory activity [1D$_{50}$ ($\mu$g/ml)] | | | | |
| | beta-Lactamase-producing | Compound | | | |
| | Strain | Ia | Ib | Ig | Ih |
| | Staphylococcus aureus 1840 | 0.055 | 0.24 | 0.36 | 1.0 |
| | Escherichia coli TN 713 | 0.0016 | 0.0001175 | 0.010 | 0.017 |
| | Enterobacter cloacae TN 1282 | 0.0050 | 0.0152 | 0.030 | 0.0032 |
| | Proteus vulgaris GN 4413 | 0.00105 | 0.00055 | 0.017 | 0.0038 |

The compounds (I) obtained according to the present invention, as is obvious from the above antimicrobial spectrum, exhibit antimicrobial activity against gram-positive and gram-negative bacteria. Therefore, the compounds (I) can be used for the treatment of bacterial infections in mammals (e.g. mouse, rat, dog, human being, etc.) and domestic animals (e.g. domestic fowl, duck, etc.)

To use the compounds (I) as an agent for treating, for example, E. coli infections, the compound (I) is dissolved in physiological saline solution to prepare an injectable solution which can be administered parenterally, e.g., subcutaneously or intramuscularly at a dose of 0.1 to 200 mg/kg/day, preferably 1 to 50 mg/kg/day. Also, for oral administration, the compound (I) is blended with lactose and encapsulated to prepare a capsule preparation which can be administered at a dose of 1 to 500 mg/kg/day, preferably 5 to 200 mg/kg/day.

Further, the compounds (I) obtained in accordance with the present invention can be used as a disinfectant. For example, a liquid preparation which can be prepared by dissolving the compound (I) in distilled water at a concentration of 0.01 to 1.0 w/v % or an ointment containing 0.5 to 50 mg, preferably 2 to 20 mg, the compound (I) per 1 g of white petrolatum or lanolin as a base can be used as a bactericide or disinfectant for hands, legs, eyes, ears, etc. of the above animals.

The compounds (I) exhibit a beta-lactamase inhibitory activity and, therefore, markedly increase the sensitivity of penicillin- or cephalosporin-resistant bacteria to ampicillin or cefotiam due to its ability to produce beta-lactamase. Accordingly, the compounds (I) can be used for treatment of infections in mammals (for example, mouse, rat, dog, human being) and avian species (for example, domestic fowl, duck), in particular, bacterial infections due to beta-lactam antibiotic-resistant bacteria, in combination with penicillin or cephalosporin antibiotics.

When the compound (I) is used in combination with other beta-lactam type agents for the treatment of infections by, for example, beta-lactam antibiotic-resistant *E. coli*, equal amounts of the compounds (I) and ampicillin are dissolved in physiological saline to prepare an injectable solution which can be administered parenterally, e.g., subcutaneously or intramuscularly, at a dose of 0.1 to 20 mg/kg/day, preferably 0.5 to 5 mg/kg/day. The compound (I) can also be administered orally at a dose of 1 to 200 mg/kg/day, preferably 5 to 100 mg/kg/day as capsules each containing an equal proportion of the compound (I) and cephalexin.

When the compound (I) is used as disinfectant, a liquid preparation, for example, an aqueous solution containing the compound (I) at a concentration of 0.1 to 10 W/V % and benzylpenicillin at a concentration of 0.1 to 1.0 W/V %, or an ointment containing 5 to 20 mg of the compound (I) and 5 to 20 mg of benzylpenicillin per 1 g of white petrolatum or lanolin as a base can be used as a bactericide or disinfectant for hands, legs, eyes, ears, etc. of the above animals.

The compounds (I) are also expected to be very useful as an intermediate for the synthesis of novel types of pharmaceuticals. The compounds of the present invention are stable in aqueous solution in a neutral pH region.

The following production example and example illustrate in more particular the practice of the present invention, but are not intended to limit it. The term "percent" in the production example designates weight/volume %, unless otherwise specified.

PRODUCTION EXAMPLE 1

Streptomyces sp. C-19393 (FERM-P No. 4774, IFO 13886, ATCC 31486, NRRL 15037) was grown on 200 ml of T culture medium [the medium comprises 2% oatmeal, 2% tomato paste, 0.2% bovril (manufactured by Bovril, England) and 2% agar and has a pH of 7.0] in a one-liter conical flask to cause sporulation. The spores were suspended in sterile water to a viable count of $1.2 \times 10^8$/ml. The spore suspension was diluted 10-fold with sterile water and 1 ml of the dilution was used to inoculate 40 ml of a seed medium in a 200-ml conical flask, which was incubated at 28° C. on a rotary shaker for 2 days. The resulting culture fluid was transferred to a 2-liter Sakaguchi shake flask containing 500 ml of the same seed medium as above and cultivated at 28° C. on a reciprocating shaker for 2 days. The culture was further transferred to a 200-liter stainless steel fermenter containing 100 liters of said seed medium supplemented with 50 ml of Actocol (Takeda Chemical Industries, Ltd., Japan) and cultivated at 28° C., 70 liters/min aeration and 150 r.p.m. for 2 days. Then, the culture was transferred to a 6-m³ fermenter containing 4 m³ of a main culture medium and grown at 30° C., 2800 liters/min aeration and 150 r.p.m. for 3 days. The seed medium mentioned above contains per liter 20 g of glucose, 30 g of soluble starch, 10 g of raw soybean flour, 10 g of corn steep liquor, 5 g of Polypepton (Daigo Nutritive Chemicals, Ltd.), 5 g of sodium chloride and 3 g of precipitated calcium carbonate (adjusted to pH 7.0 before sterilization). The main culture medium contained per liter 30 g of glucose, 30 g of soluble starch, 15 g of raw soybean flour, 15 g of cottonseed flour, 0.25 g of potassium dihydrogen phosphate, 0.6 g of potassium monohydrogen phosphate, 0.002 g of cobalt chloride and 0.5 g of Actoccol (adjusted to pH 7.0 before sterilization). These media were all steam-sterilized at 120° C. for 20 minutes. The fermentation broth thus obtained was filtered with Hyflo-Supercel (Johns Manville Co., U.S.A.) and the filtrate (4000 l) was adjusted to pH 6.3 and passed through a column of Amberlite IRA-402 (Cl⁻-form, Rohm and Haas Co., U.S.A.). After washing the column with 200 l of 0.02M aqueous NaCl, elution was carried out with 1000 l of 1.5M NaCl. The eluate was passed through a column of HP-20 (70 l) and the antibiotic activity was eluted with 280 l of water. The eluate was passed through a column of activated carbon (15 l) and after washing the column with 45 l of water, the antibiotic activity was eluted with 60 l of 7% isobutanol. The eluate was concentrated to 10 l and 500 g of NaCl was added to the residue. The mixture was passed through a column of HP-20 (6 l) and elution was carried out with 36 l of 5% NaCl. The eluate was passed through a column of activated carbon (3 l). The column was washed with 7.5 l of water and, then, elution was carried out with 8% isobutanol. The eluate was concentrated to 8 l under reduced pressure and, then, passed through a column of Diaion WA-30 (acetate-form, Mitsubishi Chemical Industries, Japan) (500 ml). The column was washed with 2.5 l of 0.2M acetic acid-sodium acetate buffer and the activity was eluted with 5 l of 1M NaCl in the same buffer.

The eluate was passed through an activated carbon column (500 ml). After the column was washed with 5% NaCl, elution was carried out with 2.5 l of 5% aqueous NaCl-methanol (4:1). The methanol was distilled off under reduced pressure and the residue was passed again through a carbon column (200 ml). The column was washed with 600 ml of $H_2O$ and 600 ml of 20% aqueous methanol, followed by elution with 600 ml of 8% isobutanol. The eluate was concentrated under reduced pressure, the residue was treated with acetone and the resultant powder was collected (580 mg). The powder was dissolved in a small amount of water and passed through a column of Amberlite XAD-II (100–200 mesh, Rohm and Haas Co., U.S.A.) (360 ml). Fractional elution was carried out with water and the active fractions were pooled, concentrated to dryness, and treated with acetone to give 100 mg of powder. The powder was dissolved in a small amount of water and passed through a column of Sephadex QAE-25 (Cl⁻-form) (40 ml). Elution was carried out with 0.04M phosphate buffer and the active fractions were pooled and subjected to liquid chromatography as described hereinbefore. The fractions giving a single peak were pooled and passed through a column of 10 ml activated carbon. The carbon column was washed with 30 ml of water and the activity was eluted with 50 ml of 8% isobutanol. The eluate was concentrated to dryness and acetone was added to the concentrate. The above procedure gave 20 mg of C-19393 $E_5$ sodium salt.

PRODUCTION EXAMPLE 2

Crude powder (30% of purity, 8 mg) of Antibiotic C-19393 $H_2$ sodium salt was dissolved in 10% aqueous methanol (10 ml), and the solution was added to a mixture of 10% aqueous methanol (10 ml) and 10% palladium-carbon (20 mg) into which hydrogen had been introduced in advance for 30 minutes. Then, hydrogen was introduced into the resultant mixture at room temperature under 1 atmospheric pressure for 3 hours to carry out reduction, and the catalyst was then filtered out, followed by concentrating the filtrate under vacuum to 2 ml of volume. The concentrated solution was passed through a column (10 ml) of XAD-II(100 to 200 mesh), and the objective compound was adsorbed on the adsorbent. After the column was washed with water (50 ml), elution was carried out with 20% methanol-water, and the fractions containing the objective compound were collected. Methanol of the active fractions was distilled off and the residue was freeze dried, thereby yielding 1.0 mg of powder of sodium [5R, 6R]-3-[(E)-2-acetamideethenylthio]-6-[1-hydroxy-1-methylethyl]-7-oxo-1-azabicyclo [3,2,0]hept-2-en-2-carboxylate.

UV: λmax ($H_2O$) 229 and 310 nm.

IR: νmax (KBr) 1760, 1620 cm$^{-1}$.

Thin layer chromatography [Cellulose f (Tokyo Kasei Co. Ltd.)]: Rf=0.87.

(Solvent system: propanol: water=4:1) High performance liquid chromatography (Manufactured by Waters Associates Inc., U.S.A.): Rt=8.2 min. [microbondapak $C_{18}$/14% methanol-0.02M phosphate buffer (pH 6.3), 2 ml/min/cm (2000 psi)], wherein Rt of the starting compound under the same conditions was 4.3 min.

NMR: δ(100 MHz, $D_2O$, TMS): 1.33(3H,s,$C_8$—$CH_3$), 1.44(3H,s, $C_8$—$CH_3$), 2.10(3H,s,$COCH_3$), 3.03(1H,dd,J=10,19,$C_4$—H),
3.85(1H,dd,J=10.5,19,$C_4$—H), 3.72(1H,d,J=6,$C_6$—H), 4.28(1H, m,$C_5$—H), 6.10(1H,d,J=14,S—CH=), 7.20(1H,d,N—CH=).

PRODUCTION EXAMPLE 3

Crude powder (30% of purity, 60 mg) of Antibiotic C-19393 $S_2$ disodium salt was dissolved in 10% aqueous methanol (20 ml), and the resulting solution was added to a mixture of 10% aqueous methanol (10 ml) and 10% palladium-carbon (20 mg) into which hydrogen had been introduced in advance for 30 minutes. Then, hydrogen was introduced into the resultant mixture at room temperature under 1 atmospheric pressure for 3 hours to carry out reduction, and the catalyst was then filtered out, followed by concentrating the filtrate under vacuum to 2 ml of volume. The concentrated solution was flown through a column (50 ml) of XAD-II (100 to 200 mesh), and the objective compound was adsorbed on the adsorbent and then eluted with water. The fractions from 45 ml to 150 ml which contained the objective compound were collected and lyophilized, whereby there was obtained 7.3 mg of powder of [5R, 6R]-3-[(E)-2-acetamidoethenylthio]-6-[1-(hydroxysulfonyloxy)-1-methylethyl]-7-oxo-1-azabicyclo[3,2,0-]hept-2-ene-2-carboxylic acid disodium salt.

UV: λmax($H_2O$) 228 and 309 nm.

IR: νmax(KBr) 1760, 1620, 1240, 1050 cm$^{-1}$.

Thin layer chromatography [Cellulose f (Tokyo Kasei Co., Ltd.)]: Rf=0.65 (sovent system: propanol:-water=4:1).

High performance liquid chromatography (Waters Associates Inc.): Rt=4.4 min. [Microbondapak $C_{18}$/14% methanol-0.02M-phosphate buffer (pH 6.3), 2 ml/min/cm (200 psi)], wherein Rt of the starting compound under the same conditions was 2.2 min.

NMR: δ(100 MHZ, $D_2O$, TMS): 1.63(3H,S,$C_8$—$CH_3$), 1.70(3H,S,$C_8$—$CH_3$), 2.10(3H,S,$COCH_3$), 3.05(1H,dd,J=10,19,$C_4$—H),
3.82(1H,dd,10.5,19,$C_4$—H), 3.88(1H,d,J=6,$C_6$—H), 4.20(1H,m,$C_5$—H), 6.10(1H,d,J=14,S—CH=), 7.20(1H,d,N—CH=).

PRODUCTION EXAMPLE 4

(1) The compound obtained according to Production Example 3 (IIh, 100 mg) was dissolved in methanol (50 ml) followed by addition of m-chloroperbenzoic acid (78 mg). The mixture was stirred at 0°–5° C. for 30 minutes. The reaction mixture was then added to 0.02M phosphate buffer (pH 6.3, 100 ml) and concentrated. The concentrate (50 ml) was washed with ethyl acetate (50 ml) and the water layer was chromatographed on an HP-20 column (100–200 mesh, 100 ml) pretreated with a 5% aqueous solution of sodium chloride using methanol-5% NaCl (5:95) as an eluent. The fraction containing the product compound was detected by HPLC, desalted by carbon chromatography and lyophilized to give [5R, 6R]-3-[(E)-2-acetamidoethenyl-(S)-sulfinyl]-6-[1-hydroxysulfonyloxy-1-methylethyl]-7-oxo-1-azabicyclo-(3,2,0)-hept-2-ene-2-carboxylic acid disodium salt (IIk, 37.2 mg).

(2) The compound obtained according to Production Example 3 (IIh, 2 mg) was dissolved in acetonitrile (6 ml) followed by addition of 12% aqueous hydrogen peroxide (4 ml). The mixture was stirred at room temperature for 2 hours. HPLC of the reaction mixture revealed a peak of product compound (IIk) according to (1) in a yield of 22%.

Thin-layer chromatography (hereinafter, briefly TLC) [cellulose f (Tokyo Kasei, Japan)]: Rf=0.38 (solvent system: propanol-water=4:1).

HPLC: Rf=1.6 min. [Radial Pak A, 2 ml/min. (the same applies hereinafter), 8% methanol-0.02M phosphate buffer (pH 6.3; hereinafter briefly, P.B.)].

UV: $\lambda_{max}^{H_2O}$nm ($E_{1cm}^{1\%}$)=250(298) and 288.5(251)

CD: $[\Lambda]_{nm}^{H_2O}$ 240(ϵ-56900) and 290(+32900)

IR: $\nu_{max}^{KBr}$ 1760, 1700, 1255, 1050 cm$^{-1}$

PMR: δ(100 MHz, $D_2O$, TMS-; the same applies hereinafter; 166, 173(3Hx2,s,8—$CH_3$), 215(3H,s,NHCO$CH_3$), 3.19 and 3.91(1Hx2,dd,$H_4$), 3.93(1H,d,$H_6$), 6.44(1H,d,S—CH=), 7.65(1H,d,N—CH=) ppm.

PRODUCTION EXAMPLE 5

The compound obtained according to Production Example 2 (IIg, 76 mg) was dissolved in methanol (38 ml) followed by addition of m-chloroperbenzoic acid (70 mg). The mixture was stirred at 0°–5° C. for 30 minutes. To this reaction mixture was added water (40 ml) and the mixture was adjusted to pH 6.3 with phosphate buffer, concentrated and washed with ethyl acetate. The water layer was chromatographed on an HP-20 (100 ml) column and eluted with water. The fraction containing the product compound was concentrated and lyophilized to give sodium [5R, 6R]-3-[(E)-2-acetamidoethenyl-(S)-sulfinyl]-6-[1-hydroxy-1-methylethyl]-7-oxo-1-azabicyclo(3,2,0)-hept-2-ene-2-carboxylate (IIj, 25 mg).

TLC: Rf=0.64

HPLC: Rt=3.8 min. [8% methanol-P.B.]

UV: $\lambda_{max}^{H2O}$nm $(E_{1cm}^{1\%})=249(476)$ and 285(354).

IR: $\nu_{max}^{KBr}$ 1770, 1700, 1630cm$^{-1}$.

CD: $[\theta]_{nm}^{H2O}$ 240($\epsilon$-55000) and 287(+10100).

PMR: 1.34, 1.45(3Hx2,s,8—CH$_3$), 2.15(3H,s,NHCOCH$_3$), 3.14, 3.83(1Hx2,dd,H$_4$), 3.84(1H,d,H$_6$), 6.31(1H,d,S—CH=), 7.56(1H,d,N—CH=).

EXAMPLE 1

(1) Compound IIb (50 mg) was dissolved in water (20 ml) and extracted with 1% tri-n-octylmethylammonium chloride in dichloromethane (20 ml). The extract was allowed to stand at room temperature for 3 days, after which the product compound was re-extracted into a 0.375% solution of sodium iodide (20 ml). The water layer was concentrated and chromatographed on an HP-2 (100–200 mesh, 30 ml) column pretreated with 5% aqueous NaCl, elution being carried out with 5% aqueous NaCl and water. The product compound was detected by HPLC and the fractions giving a single peak were pooled, concentrated and lyophilized to give [5R, 6R]-3-[(Z)-2-acetamidoethenyl-(R)-sulfinyl]-6-(1-hydroxysulfonyloxy-1-methylethyl)-7-oxo-1-azabicyclo(3,2,0)-hept-2-ene-2-carboxylic acid disodium salt (Ib, 24.4 mg).

HPLC: 8% methanol-0.02M phosphate buffer (pH 6.3), 2 ml/min. (Except for the concentration of methanol, the same conditions apply hereinafter): Rt=5.9 min. (Rt of IIb=3.1 min.).

UV: $\lambda_{max}^{H2O}$nm $(E_{1cm}^{1\%})=241.5(310)$ and 292.5(215).

IR: $\nu_{max}^{KBr}$ 1770, 1630, 1250, 720cm$^{-1}$.

PMR(100 MHz): $\delta_{ppm}^{D2O}$ 1.66 δ1.73(8-(CH$_3$)$_2$, each 3H), 5.90(S—CH=, 1H,d,J=8 Hz), 7.39(N—CH=,1H,d,J=8 Hz).

(2) Compound IIb (42 mg) was dissolved in water (10 ml) and extracted with 1% tri-n-octylmethylammonium chloride in dichloromethane (20 ml). The extract was refluxed for 8 hours and after cooling, the product compound was re-extracted into a 0.75% solution of sodium iodide (20 ml). The water layer was worked up as above (1) to give the disodium salt of compound Ib (19.3 mg).

(3) Compound IIb (100 mg) was dissolved in water (50 ml) and extracted with 1% tri-n-octylmethylammonium chloride in chloroform (50 ml). The extract was refluxed for 1.5 hours. HPLC showed a peak of the product compound in a yield of 88%. The product compound was re-extracted into a 0.75% solution of sodium iodide (25 ml). The water layer was concentrated, the concentrate was chromatographed on an HP-20 (100–200 mesh, 125 ml) column, and elution was carried out with water. The fraction containing the product compound was concentrated and the residue was treated with acetone to give the disodium salt of Ib as powders (56.5 mg).

(4) Compund IIb was reacted using the different combinations of quaternary ammonium halide and solvent under various conditions as set forth in Table 3 and the reaction mixtures worked up in the same manner as above (1). In all cases, the product compound (Ib) was assayed by HPLC. The results are shown in Table 3. (In all cases, the concentration of starting compound IIb was 200 μg/ml).

TABLE 3

| Halide* | Solvent | Temperature (°C.) | Time (hrs.) | Yield (%) |
|---|---|---|---|---|
| (1) | Dichlormethane | 40 | 8 | 93 |
| " | Chloroform | 61 | 1 | 85 |
| " | 1,2-Dichloroethane | 60–62 | 0.5 | 61 |
| " | 1,1,1-Trichloroethane | 74 | 1 | 43 |
| " | Benzene | 81 | 1 | 23 |
| " | Ethyl acetate | 60–62 | 3 | 25 |
| (2) | Dichloromethane | 40 | 6 | 77 |
| (3) | " | 40 | 16 | 76 |
| (4) | Chloroform | 61 | 2 | 55 |
| (5) | " | 61 | 2 | 40 |

EXAMPLE 2

(1) Compound IIa (30 mg) was dissolved in dimethylformamide (3 ml) followed by addition of 2% tri-n-octylmethylammonium chloride in dichloromethane (300 ml). The solution was refluxed for 8 hours and, after cooling, the product compound was extracted into a 3% solution of sodium iodide (150 ml). HPLC showed a peak of product compound in a yield of 82%. The water layer was concentrated, the concentrate was chromatographed on an HP-20 (100–200 mesh, 30 ml) column, and elution was carried out with water. The fraction containing the product compound was concentrated and lyophilized to give sodium [5R, 6R]-3-[(Z)-2-acetamidoethenyl-(R)-sulfinyl]-6-[1-hydroxy-1-methylethyl]-7-oxo-1-azabicyclo(3,2,0)-hept-2-ene-2-carboxylate (Ia, 19.8 mg).

HPLC: 15% methanol, Rt=7.5 min. (Rt of IIa=3.6 min.).

UV: $\lambda_{max}^{H2O}$nm $(E_{1cm}^{1\%})$ 239(367) and 295(255).

IR: $\nu_{max}^{KBr}$ 1765, 1630, 1260, 1000cm$^{-1}$.

PMR: $\delta_{ppm}^{D2O}$ 1.34 and 1.45(8-(CH$_3$)$_2$, each 3H), 5.88 (S—CH=,1H,d,J=8 Hz), 7.40(N—CH=, 1H,d,J=8 Hz).

(2) The above reaction (1) was repeated except that methanol was used in lieu of dimethylformamide. After 9 hours of reaction, HPLC revealed a peak of Ia in a yield of 85%.

EXAMPLE 3

Compound IId (12.8 mg) was dissolved in water (10 ml) and extracted with 1% tri-n-octylmethylammonium chloride in dichloromethane (10 ml). The extract was refluxed for 8 hours. HPLC showed a peak of product compound in a yield of 88%. The reaction mixture was re-extracted three times with a 0.375% aqueous solution of sodium iodide (10 ml). The second extract only was concentrated, the concentrate was chromatographed on an HP-20 (100–200 mesh, 60 ml) column, and elution was carried out with water. The eluate was concentrated and lyophilized to give [5R, 6R, 8S]-3-[(Z)-2-acetamidoethenyl-(R)-sulfinyl]-6-[1-hydroxysulfonyloxyethyl]-7-oxo-1-azabicyclo(3,2,0)-hept-2-ene-2-carboxylic acid disodium salt (Id, 3.2 mg).

HPLC: 4% methanol, Rt=4.8 min. (Rt of IID=2.3 min.).

UV: $\lambda_{max}^{H2O}$ $(E_{1cm}^{1\%})=242(281)$ and 290(196).

IR: $\nu_{max}^{KBr}$ 1770, 1700, 1260, 1040cm$^{-1}$.

PMR: 1.55(8—CH$_3$,d,J=6 Hz), 5.90(S—CH=,d,J=8 Hz), 7.39(N—CH=,d,J=8 Hz).

EXAMPLE 4

Compound IIc (15 mg) was dissolved in water (200 ml) and extracted with 2% tri-n-octylmethylammonium chloride in chloroform (200 ml). The extract was refluxed for 2 hours, after which the reaction product was re-extracted into a 3% aqueous solution of sodium iodide (50 ml). HPLC showed a peak of reaction product in a yield of 78%. The water layer was worked up in the same manner as Example 2-(1) to give sodium [5R, 6R, 8S]-3-[(Z)-2-acetamidoethenyl-(R)-sulfinyl]-6-[1-hydroxy-ethyl]-7-oxo-1-azabicyclo(3,2,0)-hept-2-ene-2-carboxylate (Ic, 6.6 mg).

HPLC: 8% Methanol, Rt=5.5 min. (Rt of IIc=2.8 min.).
UV: $\lambda_{max}^{H2O}$nm (E$_{1cm}^{1\%}$)=238 (330) and 291(228).
IR: $\nu_{max}^{KBr}$ 1770, 1630, 1260cm$^{-1}$.
PMR: $\delta_{ppm}^{D2O}$ 1.38(8—CH$_3$,d,J=6 Hz), 5.90(S—C$\underline{H}$=,d,J=8 Hz), 7.40(N—C$\underline{H}$=,d,J=8 Hz)

EXAMPLE 5

Compound IIe (64 mg) was dissolved in water (1.28 l) and extracted with 2.5% tri-n-octylmethylammonium chloride in chloroform (1.28 l). The extract was refluxed for an hour and, after cooling, the product compound was reextracted into a 7.5% solution of sodium iodide (160 ml). HPLC showed a peak of reaction product in a yield of 95%. The water layer was worked up in the same manner as Example 2-(1) to give sodium [5R, 6R, 8S]-2-[(Z)-2-acetamidoethenylthio]-6-[1-hydroxy-ethyl]-7-oxo-1-azabicyclo(3,2,0)-hept-2-ene-2-carboxylate (Ie, 33 mg).

HPLC: 6% methanol, Rt=11.6 min. (Rt of IIe=6.8 min.).
UV: $\lambda_{max}^{H2O}$nm (E$_{1cm}^{1\%}$)=226(320) and 306(268).
IR: $\nu_{max}^{KBr}$ 1755, 1630, 1265cm$^{-1}$.
PMR: $\delta_{ppm}^{D2O}$ 1.35 (8—CH$_3$,d,J=6Hz), 5.74(S—C$\underline{H}$=,d,J=7.5 Hz), 7.20(N—C$\underline{H}$=,d,J=7.5 Hz).

EXAMPLE 6

Compound IIf (20.9 mg) was dissolved in water (10 ml) and extracted with 1% tri-n-octylmethylammonium chloride in dichloromethane (10 ml). The extract was refluxed for 9 hours and after cooling, the reaction product was reextracted into a 0.375% solution of sodium iodide (10 ml). HPLC showed a peak of reaction product in a yield of 95%. The water layer was concentrated, the concentrate was chromatographed on an HP-20 (100–200 mesh, 130 ml) column, and elution was carried out with water and 5% aqueous methanol. The fraction containing the product compound was concentrated and lyophilized to give [5R, 6R, 8S]-3-[(Z)-2-acetamidoethenylthio]-6-[1-hydroxysulfonyloxyethyl]-7-oxo-1-azabicyclo(3,2,0)-hept-2-ene-2-carboxylic acid disodium salt (If, 8.8 mg).

HPLC: 4% methanol, Rt=5.2 min. (Rt of IIf=4.1 min.).
UV: $\lambda_{max}^{H2O}$nm (E$_{1cm}^{1\%}$)=228(291) and 307(179).
IR: $\nu_{max}^{KBr}$ 1750, 1620, 1260, 1035cm$^{-1}$.
PMR: $\delta_{ppm}^{D2O}$ 1.50(8—CH$_3$,d,J=6 Hz), 5.74(S—C$\underline{H}$=,d,J=8 Hz), 7.21(N—C$\underline{H}$=,d,J=8 Hz)

EXAMPLE 7

Compound IIg (10 mg) was dissolved in water (200 ml) and extracted with 2% tri-n-octylmethylammonium chloride in dichloromethane (200 ml). The extract was refluxed for 8 hours and the product compound was re-extracted into a 3% solution of sodium iodide (50 ml). The water layer was worked up in the same manner as Example 2-(1) to give sodium [5R, 6R]-3-[(Z)-2-acetamidoethenyl-thio]-6-[1-hydroxy-1-methyl-ethyl]-7-oxo-1-azabicyclo(3,2,0)-hept-2-ene-2-carboxylate (Ig, 7 mg). In TLC, HPLC, UV, IR, and PMR, this compound Ig was identified with the authentic sample.

EXAMPLE 8

Compound IIh (40 mg) was dissolved in water (20 ml) and extracted with 1% tri-n-octylmethylammonium chloride in chloroform (20 ml). The extract was refluxed for 2 hours and the reaction product was re-extracted into a 0.75% solution of sodium iodide (10 ml). The water layer was worked up in the same manner as Example 1-(3) to give [5R, 6R]-3-[(Z)-2-acetamido-ethenyl-thio]-6-[1-hydroxysulfonyloxy-1-methyl-ethyl]-7-oxo-1-azabicyclo(3,2,0)-hept-2-ene-2-carboxylic acid disodium salt (Ih, 31 mg). In TLC, HPLC, UV, IR and PMR, this compound Ih was identified with the authentic sample.

EXAMPLE 9

Compound IIi (130 mg) was dissolved in water (2.0 l) and extracted with 2% tri-n-octylmethylammonium chloride in chloroform (20 ml). The extract was refluxed for 1.5 hours and after cooling, the product compound was re-extracted into a 6.6% solution of sodium iodide (375 ml). HPLC showed a peak of product compound in a yield of 93%. The water layer was worked up in the same manner as Example 2-(1) to give sodium [5R, 6S, 8S]-3-[(Z)-2-acetamidoethenyl-thio]-6-[1-hydroxy-ethyl]-7-oxo-1-azabicyclo(3,2,0)-hept-2-ene-2-carboxylate (Ii, 64 mg).

HPLC: 10% methanol, Rt=14.0 min. (Rt of IIi=6.7 min.).
UV: $\lambda_{max}^{H2O}$nm (E$_{1cm}^{1\%}$)=231(390) and 308(344).
IR: $\nu_{max}^{KBr}$ 1755, 1620, 1400, 1265cm$^{-1}$.
PMR: $\delta_{ppm}^{D2O}$ 1.70(8—CH$_3$,d,J=6 Hz), 5.70(S—C$\underline{H}$=,d,J=8 Hz), 7.16(N—C$\underline{H}$=,d,J=8 Hz).

EXAMPLE 10

The compound obtained in Production Example 5 (IIj, 7 mg) was dissolved in water (140 ml) and extracted with 2% tri-n-octylmethylammonium chloride in chloroform (140 ml). The extract was refluxed for 3 hours and after cooling, the product compound was re-extracted into a 1.5% solution of sodium iodide (100 ml). HPLC showed a peak of reaction product in a yield of 83%. The water layer was worked up in the same manner as Example 2-(1) to give sodium [5R, 6R]-3-[(Z)-2-acetamidoethenyl-(S)-sulfinyl]-6-[1-hydroxy-1-methyl-ethyl]-7-oxo-1-azabicyclo(3,2,0)-hept-2-ene-2-carboxylate (Ij, 5 mg).

TLC: Rf=0.64.
HPLC: Rt=4.2 min. [8% methanol-P.B.].
UV: $\lambda_{max}^{H2O}$nm (E$_{1cm}^{1\%}$)=237(408) and 290(262).
IR: $\nu_{max}^{KBr}$ 1765, 1705, 1635, 1385, 1270, 1020cm$^{-1}$.
CD: $[\theta]_{nm}^{H2O}$ 235($\epsilon$-22700) and 286(+32800).
PMR: 1.32, 1.41(3Hx2,s,8—CH$_3$), 2.15(3H,s,NHCOCH$_3$), 3.22, 3.83(1Hx2,dd,H$_4$), 3.82(1H,d,H$_6$), 5.71(1H,d,S—C$\underline{H}$=), 7.27(1H,d,N—C$\underline{H}$=).

EXAMPLE 11

The compound obtained in Production Example 4 (IIk, 10 mg) was dissolved in water (10 ml) and extracted with 1% tri-n-octylmethylammonium chloride in chloroform (10 ml). The extract was refluxed for 3 hours and after cooling, the product compound was re-extracted into a 0.75% solution of sodium iodide (10 ml). HPLC showed a peak of reaction product in a yield of 88%. The water layer was chromatographed on an HP-20 (100–200 mesh, 20 ml) column pretreated with 5% NaCl and elution was carried out with 5% aqueous NaCl and methanol-5% aqueous NaCl (3:97). The fractions containing the product compound were pooled and concentrated. The concentrate was chromatographed on a column of activated carbon (5 ml) and the product compound was eluted with 8% aqueous isobutanol and N/50 aqueous ammonia-8% aqueous isobutanol (2:98). The eluate was concentrated and lyophilized to give [5R, 6R]-3-[(Z)-2-acetamidoethenyl-(S)-sulfinyl]-6-[1-hydroxysulfonyloxy-1-methyl-ethyl]-7-oxo-1-azabicyclo(3,2,0)-hept-2-ene-2-carboxylic acid disodium salt (Ik, 8.4 mg).

TLC: Rf=0.30.

HPLC: Rt=1.8 min. (3% methanol-P.B.).

UV: $\lambda_{max}^{H2O}(E_{1cm}^{1\%})=237(276)$ and $292(188)$.

CD: $[\theta]_{nm}^{H2O}$ 232($\epsilon$-12900) and 282(+31400).

IR: $\nu_{max}^{KBr}$ 1765, 1700, 1260, 1050cm$^{-1}$.

PMR: $\delta$1.65, 1.68(3Hx2,s,8—CH$_3$), 2.17(3H,s,NHCOC$\underline{H}_3$), 3.26 and 3.92(1Hx2,dd,H$_4$), 3.98(1H,d,H$_6$), 5.85(1H,d,S—C$\underline{H}$=), 7.30(1H,d,N—C$\underline{H}$=)

What we claim is:

1. A process for the production of a compound of the formula

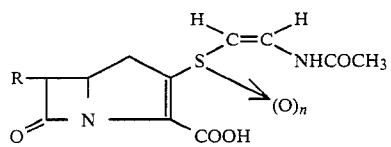

wherein R is a group of the formula

wherein

R$_1$ is H or methyl,

R$_2$ is (1) H, (2) OH, (3) R$_3$COO— in which R$_3$ is R$_4$ or —NHR$_4$ wherein R$_4$ is (a) alkyl of 1 to 6 carbons, (b) alkenyl of up to 6 carbons, (c) phenyl, or (d) alkyl of 1 to 6 carbons substituted by phenyl, lower alkyl phenyl, C$_{1-4}$ alkoxyphenyl, halophenyl or phenyloxy or (4) R$_5$O$_3$SO— wherein R$_5$ is H or lower alkyl, and n is 0 or 1 or a phsiologically acceptance salt thereof which comprises subjecting a compound of the formula

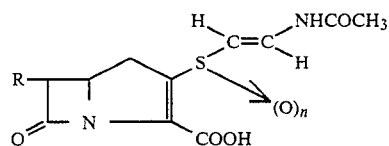

wherein R and n are as defined above to isomerization by treatment in an organic solvent which is nonpolar or of weak polarity or such solvents containing a small proportion of an organic solvent of strong polarity, said treatment being with a chloride or bromide of a quaternary ammonium compound having a total of 18 to 30 carbon atoms for the four substituents, the treatment being carried out at a temperature of from about room temperature up to about the boiling point of the solvent.

2. The process as claimed in claim 1, wherein the quaternary ammonium halide is used in a stoichiometric excess based on a starting compound.

3. The process as claimed in claim 1, wherein the organic solvent is a halogenated hydrocarbon.

* * * * *